(12) United States Patent
Török et al.

(10) Patent No.: US 9,713,570 B2
(45) Date of Patent: Jul. 25, 2017

(54) MOBILE APPARATUS FOR THE DISPERSION AND TRANSDERMAL DELIVERY OF PHARMACEUTICAL, MEDICAL OR PURIFIED CARBON DIOXIDE GAS

(75) Inventors: Péter Török, Szigetszentmiklos (HU); József Török, Budapest (HU); Tamás Török, Budapest (HU); Karsa Tímea, legal representative, Kistarcsa (HU)

(73) Assignee: Respiderm Corporation, Little Rock, AR (US)

( * ) Notice: Subject to any disclaimer, the term of this patent is extended or adjusted under 35 U.S.C. 154(b) by 937 days.

(21) Appl. No.: 12/936,775

(22) PCT Filed: Apr. 9, 2008

(86) PCT No.: PCT/US2008/004543
§ 371 (c)(1),
(2), (4) Date: Feb. 7, 2012

(87) PCT Pub. No.: WO2009/126121
PCT Pub. Date: Oct. 15, 2009

(65) Prior Publication Data
US 2012/0172788 A1    Jul. 5, 2012

(51) Int. Cl.
*A61M 37/00* (2006.01)
*A61H 33/00* (2006.01)
(Continued)

(52) U.S. Cl.
CPC ........... *A61H 33/60* (2013.01); *A61H 9/0078* (2013.01); *A61H 35/00* (2013.01); *A61M 35/00* (2013.01);
(Continued)

(58) Field of Classification Search
CPC ............... A61M 35/00; A61M 35/003; A61M 2202/0225; A61H 35/00; A61H 35/006; A61H 2033/145; A61H 33/14
(Continued)

(56) References Cited

U.S. PATENT DOCUMENTS 2,925,716 A * 2/1960 Regan ...................... F23R 3/18
60/749
5,945,039 A * 8/1999 Kojima ...................... 261/36.1
(Continued)

FOREIGN PATENT DOCUMENTS

| EP | 1 709 951 A1 | 10/2006 |
|---|---|---|
| JP | 2002-143867 | 5/2002 |
| JP | 2005-058745 A | 3/2005 |
| JP | 2007-181720 | 7/2007 |

OTHER PUBLICATIONS

European Search Report for Application No. 08742657.3 mailed Feb. 3, 2016.

*Primary Examiner* — Laura Bouchelle
*Assistant Examiner* — Anh Bui
(74) *Attorney, Agent, or Firm* — Merchant & Gould P.C.

(57) ABSTRACT

A mobile treatment apparatus for use in treating a user of the apparatus with medical or therapeutic gases, comprising a mixing unit for containing water and having a motionless mixing means; a gas cartridge unit removably mounted to the mixing unit via a cartridge piercing module, wherein a pressure-regulating valve regulates a flow rate of a gas from the cartridge through the mixing means, to achieve a specified gas-water mixture that is effective for transdermal delivery of the gas to the user; and a wearable receiver suit for forming a space around at least an area of the user's body to be treated, wherein the suit is connected to the mixing unit, for delivery of the gas to treat the area via the transdermal delivery.

20 Claims, 8 Drawing Sheets

(51) Int. Cl.
  *A61H 9/00* (2006.01)
  *A61M 35/00* (2006.01)
  *A61H 35/00* (2006.01)
  *A61H 33/02* (2006.01)
  *A61H 33/14* (2006.01)

(52) U.S. Cl.
  CPC .............. *A61H 33/02* (2013.01); *A61H 33/14* (2013.01); *A61H 35/006* (2013.01); *A61H 2033/145* (2013.01); *A61H 2201/0157* (2013.01); *A61H 2201/165* (2013.01); *A61H 2205/08* (2013.01); *A61H 2205/10* (2013.01); *A61M 35/003* (2013.01); *A61M 2202/0225* (2013.01)

(58) Field of Classification Search
  USPC ....................................... 604/24; 261/DIG. 7
  See application file for complete search history.

(56) References Cited

U.S. PATENT DOCUMENTS

| | | | | |
|---|---|---|---|---|
| 6,036,054 | A | * | 3/2000 | Grill .................... B01F 3/04808 141/64 |
| 6,164,632 | A | | 12/2000 | Uchida et al. |
| 6,905,111 | B2 | | 6/2005 | Nagasaka et al. |
| 7,152,850 | B2 | | 12/2006 | Sakakibara et al. |
| 2002/0156416 | A1 | * | 10/2002 | Stenzler .............. A61M 1/0088 604/23 |
| 2005/0254993 | A1 | * | 11/2005 | Tanaka .................. A61M 35/00 422/33 |
| 2005/0261615 | A1 | | 11/2005 | Weston |
| 2005/0279349 | A1 | * | 12/2005 | Patton ............... A61M 15/0065 128/200.14 |
| 2006/0202363 | A1 | * | 9/2006 | Ooyachi ............. B01F 3/04808 261/94 |
| 2013/0072862 | A1 | * | 3/2013 | Blackhurst ......... A61B 1/00154 604/24 |

* cited by examiner

FIG.8

MOBILE APPARATUS FOR THE DISPERSION AND TRANSDERMAL DELIVERY OF PHARMACEUTICAL, MEDICAL OR PURIFIED CARBON DIOXIDE GAS This application is a national stage entry under 35 U.S.C. §371 of PCT/US2008/004543, filed Apr. 9, 2008, and published as WO 2009/126121 on Oct. 15, 2009, the entire disclosure of PCT/US2008/004543 is hereby incorporated by reference. A claim of priority is made to PCT/US2008/004543, to the extent appropriate.

FIELD OF THE INVENTION

The present invention relates generally to an apparatus for non-invasive treatments with various therapeutic or medical gases, and more particularly, to a mobile apparatus for artificially mimicking and enhancing the positive effects of carbon dioxide ($CO_2$) balneotherapy by transdermally delivering pharmaceutical, medical or purified $CO_2$, to a user for therapeutic treatments.

BACKGROUND OF THE INVENTION

Balneotherapy (treatment through bathing) using naturally occurring carbonated water (springs containing $CO_2$) is the most thoroughly studied technique in applied balneotherapeutics. Since ancient times, physicians have observed the positive effects of "carbon dioxide springs" for bathing and drinking. Systematic balneotherapies have been practiced for more than 120 years, for treating cardiovascular (high blood pressure), diabetes mellitus, arthritis and osteoporosis conditions without side effects.

In recent years, such treatments have become solidly grounded in the natural sciences, particularly through studies in Europe. For example, in the European Union, health insurance companies have been reimbursing such treatments prescribed by physicians since 1998. However, mineral-rich springs have begun to run dry in some places around the world. Reportedly, such waters began to lose their natural color 10 years ago.

Independent studies have shown that, for therapeutic purposes, the $CO_2$ gas concentration in water needs to reach a higher level of at least 600-1000 ppm (parts per million). It has also been determined that the desired long-term effects can only be obtained through serial applications.

A key challenge for the effective therapeutic use of artificial carbonated waters has been keeping the $CO_2$ in the water during the treatment periods. That is, preventing the $CO_2$ from escaping by properly adjusting the concentration rate and evenly dispersing the $CO_2$ has posed technological barriers.

This problem results from the fact that $CO_2$ easily dissolves in water and is also easily emitted from water. These characteristics are evident upon opening carbonated drinks, such as beers or cokes. If one can artificially achieve higher concentrations (1,000 parts per million) of $CO_2$, once can expect to benefit from similar effects on physiological functions as the above-described $CO_2$ balneotherapy.

In general, however, the use of various gases such as $CO_2$ in medicine have been minimally explored. It is known that gases are important biological messenger molecules, and well-known gases and new gas pre-mixes show promising biological effects. Furthermore, naturally occurring gases seem to have low toxicity profiles. Additionally, many scientists and researchers have increasingly been tackling the problem of delivering drugs, such as $CO_2$ and other medical gases, through the skin. Such delivery needs to occur without the side effects associated, for example, with breaking the skin's natural barrier function.

Various conventional methods have been used to artificially produce carbonated spring and carbonic waters. U.S. Pat. No. 7,152,850 discloses a device for manufacturing carbonated springs, using hot water in a bath pumped up by a suction pump, as well as $CO_2$ gas supplied from a $CO_2$ gas cylinder, which are introduced into a $CO_2$ gas dissolver having a membrane module. A gas flow rate adjusting means is used to obtain a carbonated spring with a high $CO_2$ concentration.

U.S. Pat. No. 6,905,111 discloses a circulation-type apparatus, involving a circulation pump and a carbonic acid gas dissolving apparatus, where the circulation pump is a diaphragm metering pump having a self-priming ability. A portable foot bath including similar features is also shown. However, the above-mentioned devices use relatively complicated structures, such as pumps and membrane type dissolvers, that are costly to manufacture and can be inconvenient to use for both commercial and home therapies.

Japanese Patent Application Publication No. 2005-058745 A2 discloses a carbon dioxide treatment device having a carbon dioxide cylinder, a bag forming a space around a region to be treated, and a three-way valve is disposed on a tube between the cylinder and the bag. A suction pump for sucking the gas in the bag and discharging such gas to the outside is arranged on the valve. However, such an arrangement, as well as its disclosed variations, does not provide a convenient yet highly simple device requiring minimal parts, for repeatedly producing high concentrations of $CO_2$, that is dispersed evenly for optimal transdermal deliveries of the $CO_2$ without side effects.

Thus, there exists a need for an effective, simple and convenient means for artificially producing carbonated springs and carbonic waters, as well as mixtures involving various other medicinal and therapeutic gases, that is also cost effective to manufacture. As mentioned above, $CO_2$ balneotherapy has been used to treat major conditions that affect hundreds of millions of people around the globe, such as osteoporosis, arthritis, diabetes mellitus and a variety of cardiovascular conditions. Additionally, $CO_2$ can have many other natural remedy effects, including, but not limited to, improving immunological responses and neurological functions, reducing swelling, increasing microvascular circulation and skin perfusion pressure, muscular strength, eliminating migraine headaches, etc.

Therefore, what is needed is a convenient, low cost means of mimicking and enhancing the many positive effects of $CO_2$, as well as for administering other pharmaceutical medical or purified gases, for potential use in a wide range of applications in a wide variety of fields.

SUMMARY OF THE INVENTION

A mobile treatment apparatus for use in treating a user of the apparatus with medical or therapeutic gases, having a mixing unit for containing water and having a motionless mixing means; a gas cartridge unit removably mounted to the mixing unit via a cartridge piercing module, wherein a pressure-regulating valve regulates a flow rate of a gas from the cartridge through the mixing means, to achieve a specified gas-water mixture that is effective for transdermal delivery of the gas to the user; and a wearable receiver suit for forming a space around at least an area of the user's body to be treated, wherein the suit is connected to the mixing unit, for delivery of the gas to treat the area via the transdermal delivery.

It is embodied in another mode of the invention a method of treating an area of an individual user with medical or therapeutic gases, including filling a mobile therapeutic apparatus, having a mixing unit including a motionless mixing means, with water, fitting a wearable receiver suit, connected to the mixing unit, to form a space around at least an area of the user's body to be treated; removably mounting a gas cartridge to the mixing unit via a cartridge piercing module, wherein a pressure-regulating valve regulates a flow rate of a gas from the cartridge through the mixing means, to achieve a specified gas-water mixture that is effective for transdermal delivery of the gas to the user; and delivering the gas to the receiver suit, to treat the area via the transdermal delivery.

DETAILED DESCRIPTION OF THE INVENTION

Referring generally to FIGS. 1-6, an apparatus according to an aspect of the present invention is formed and operated as follows. Referring in detail to FIGS. 1-4, the apparatus consists of a mobile treatment apparatus 1 with a delivery with 2 including an elongated, fill container 3, having a static mixing chamber or unit 4 installed within the container 3. The mixing unit 4 generally comprises a number of conical shaped baffles or mixing elements 5 that are positioned in a column configuration, with each baffle above and partially overlapping the other and their circular base sides facing upwards. Narrow connecting pieces 6 at the periphery of this column position these baffles in place. A mixing tube 7, having various openings to allow inflows from a fluid in the fill container 3, surrounds these mixing elements 5, and a delivery tube 8 extends through central point holes in the conical-shaped baffles 5 to terminate in a jet delivery assembly 9 towards a bottom of the fill container 3.

The delivery tube 8 is connected to a cartridge holder tube 10, for receiving and positioning therein a suitable gas cartridge 11. A typical gas cartridge usable for the present invention may be, as an example, a gas cartridge containing 70-93 g of pure, medical grade $CO_2$, with 8 MPa of filling pressure. The $CO_2$ gas typically should have a purification level of over 90%. Naturally, the use of other suitable grade and quantities of $CO_2$ gases, or other gases usable for treatments as commonly known in the art, are also intended to fall within the scope of the present disclosure. The gas cartridge may be a disposable type, having an outlet that can be pierced to release the flow of gas. It may be a custom, specialized type or a standard cartridge similar to those typically used in soda siphons for producing carbonated beverages or seltzer waters, or for providing propulsion force in paintball guns. For example, the gas cartridge may have dimensions of 200 mm length×35 mm diameter with neck dimensions of 16 mm length×1.5 mm diameter.

Such gas cartridge may be inserted within the cartridge holder tube 10, and held in place by a cap 12 having threads 13 for engaging with threads 14 at an upper portion of the cartridge holder 10, above a flange or rim 15 of the holder 10. The cap 12 may be formed to removably surround and retain the bottom end of the cartridge 11, and may be ergonomically shaped to be easily grasped by a user, to enable the user to twistably insert the cartridge 11 into the cartridge holder tube 10, and screw the cartridge 11 into the delivery unit 2 via the threads 13, 14.

At the lower end of the cartridge holder tube 10 is installed a cartridge head holder 16 having a significantly narrower diameter than the cartridge holder 10. The interior walls of the cartridge head holder 16 may have o-rings or the like installed thereon (not shown), to further retain and support the cartridge head/neck 17 and provide sealing to prevent the entrance of the gas into the rest of the cartridge holder tube 10. Extending through the delivery tube 8 and into this cartridge head holder 16 is a narrow tubular, hollow, piercing pin 18 adapted to pierce an outlet end 19 of the head of the cartridge 11, to puncture and produce a hole through which the gas can exhaust from the gas cartridge 11. It is to be understood, however, that other means for exhausting the gas, such as other push to crack valves or other methods for releasing the flow of gas from the cartridge as commonly known the art may also be used.

Within the cartridge head holder 16 is may be disposed a pressure regulating valve (not shown) for controlling and/or reducing the pressure of the gas flow from the cartridge 11 to a specified or desired level of flow. Also located within either the above-mentioned cap 12 or in the cartridge head holder 16 may be a safety means for holding, screwing in, or "locking" in the cartridge into the delivery unit 2, such as pressure-activated locks or additional threading, to prevent its accidental ejection from the delivery unit 2 and causing injury to the user, etc. There may also be provided gas dissipation features to prevent the accidental release of the pressurized gas from contacting the user. Such methods may include providing holes in the rim 15 or the sides of the cartridge holder 10 to vent the gas jets, or installing flexible conduits at the cartridge holder 10 to redirect unintentionally released gas jets. Other means for preventing such unintended ejections or gas discharges in the event of failures in the system may be used as is commonly known in the art. All such safety means as known in the art are intended to be encompassed within the scope of the present disclosure.

Figure 2:
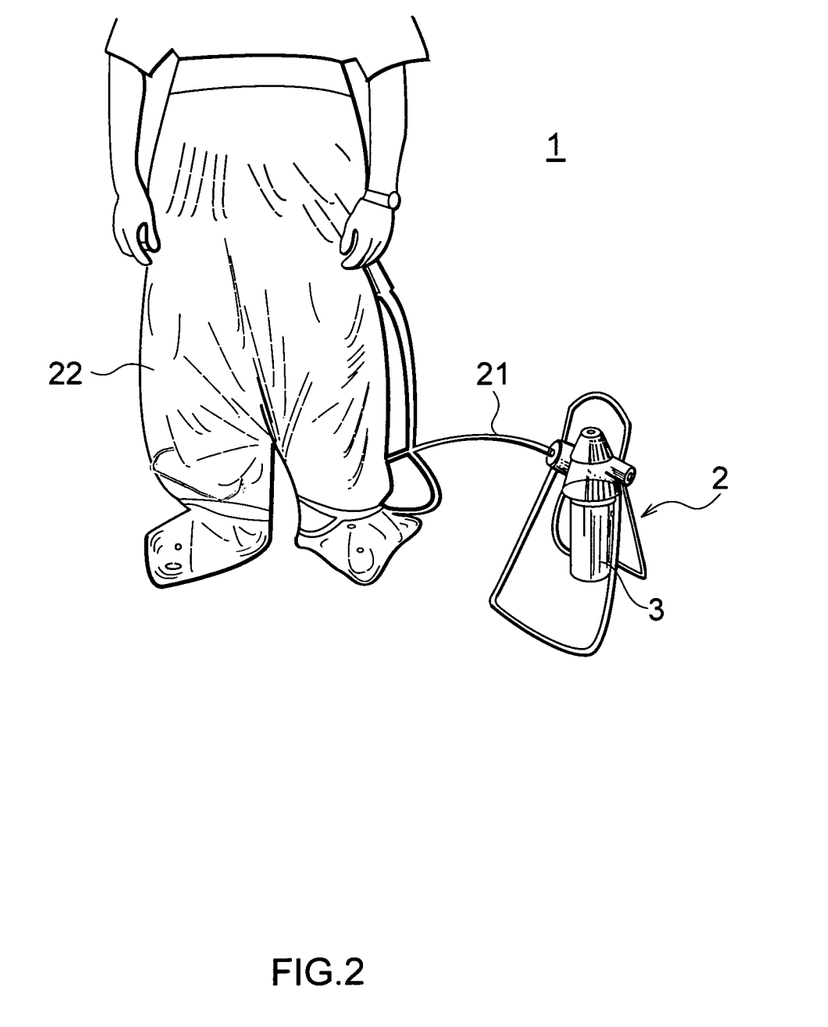
FIG. 2 is a perspective view of the complete mobile treatment apparatus of the subject invention, showing the delivery unit connected to the absorption suit worn by the user.

The fill container 3 has an inlet opening 3a that can be closed with a fill cap 20. The fill cap 20 may have a pressure relief valve such as a 2 psi valve (not shown), installed in it, as a further safety measure for avoiding an over-pressurizing of the delivery unit 2. An outlet opening 3b of the fill container 3 is connected to a flexible tubing 21 via a connecting pipe 21a. The tubing 21 is in turn adapted to be connectable to a wearable receiver or absorption suit 22, as shown in FIG. 2. Check valves at the aforementioned connection points on the tubing 21 can prevent backflows from the suit 22 to the fill container 3.

The absorption suit 22 is designed to fit to and sealably enclose a portion of the body of the user. It may be made of a sealable, wearable material for therapeutic/medical uses, such as a disposable plastic of therapeutic grade. In the present embodiment, the suit 22 is of a pants or trousers type, for covering the lower body of the user including the feet and legs, and it can be sealed off at the waist of the user by folding over any excess material at the waist and tying off that opening with the provided string.

The delivery unit 2 may also be provided with adjustable, spreadable wireform legs 23, as well as a relatedly adjustable handle 24, for the unit's easy carrying and secure, free standing positioning on the floor, etc.

In operation, the mobile treatment apparatus 1 of the present invention functions as follows. The user first removes the fill cap 20 and fills the fill container 3 with water up to a specified level. Although the present description indicates using regular tap water as the fluid, the use of other potential fluids as commonly known in the art are intended to be encompassed within the present invention. The tap water may typically have a temperature of between 35-70 C. It is important in the present invention that the piercing pin 18 and the pressure regulating valve at the lower end of the cartridge holder tube 10 be immersed in the water at the aforementioned temperatures. Such a water level is important to prevent potential ice formation at the pierced outlet 19 of the gas cartridge 11 and in the pressure regulating valve, during the outflow of the $CO_2$ gas. Such freezing may potentially reduce or stop the gas flow and cause pressure build-ups, leading to a possible explosion of the apparatus 1.

The user then replaces the fill cap 20 securely, and puts on the receiver or absorption suit 22. The user properly seals the suit on his body, connects the flexible tubing 21, and ensures that the suit 22 is intact.

The user then unscrews the cap 12 and removably secures a bottom end of the gas cartridge 11 into a hollow receiving area of the cap 12. With the delivery unit 2 standing in a stationery position with the legs 23 spread apart, the cartridge 11 is inserted into the delivery unit 2 head first until the respective threads 13, 14 of the cap 12 and the cartridge holder 10 engage.

Figure 3:
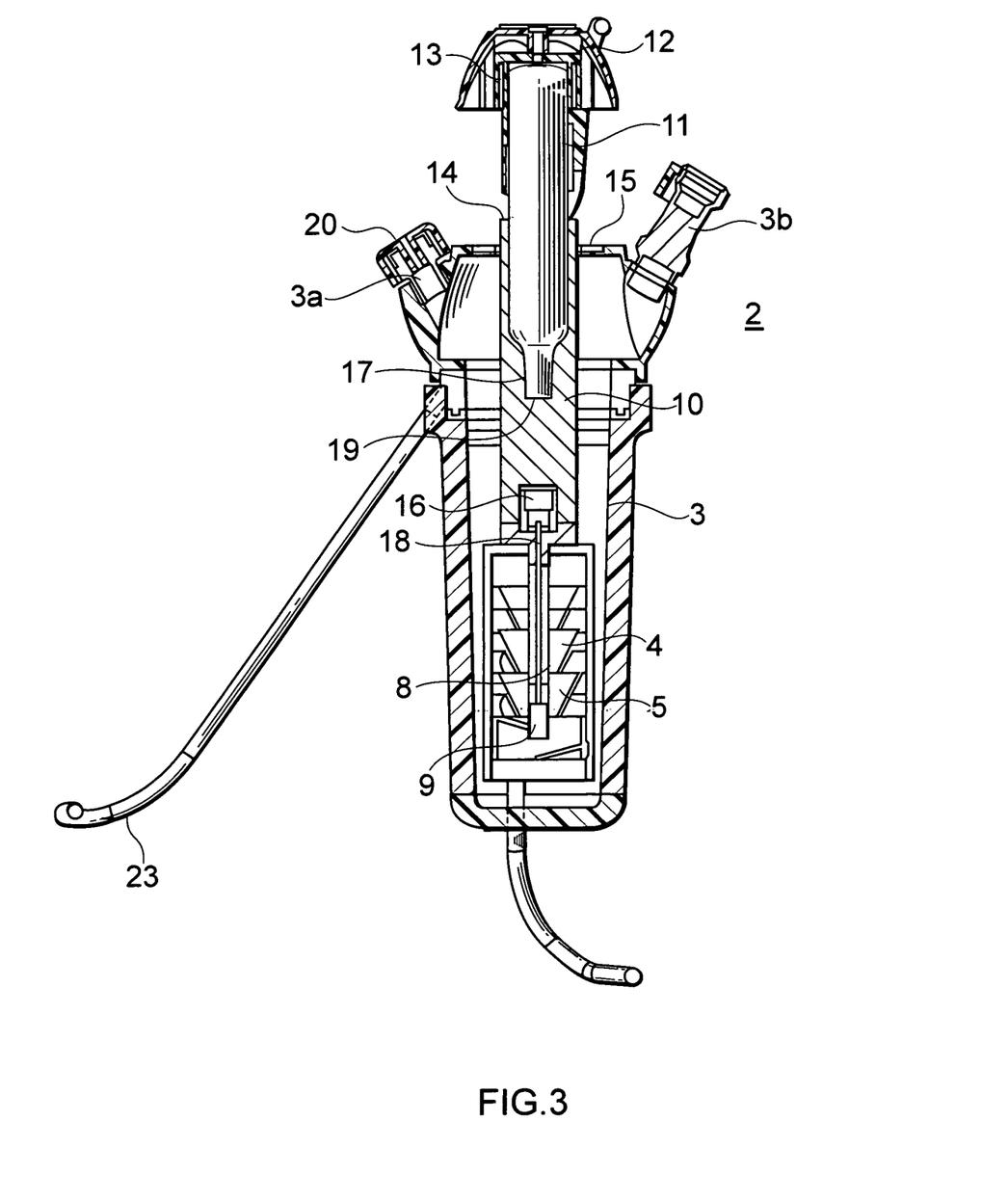
FIG. 3 is an elevational, cross-sectional view of the delivery unit shown in FIG. 1, with the gas cartridge in a partially pushed-in state.
Figure 4:
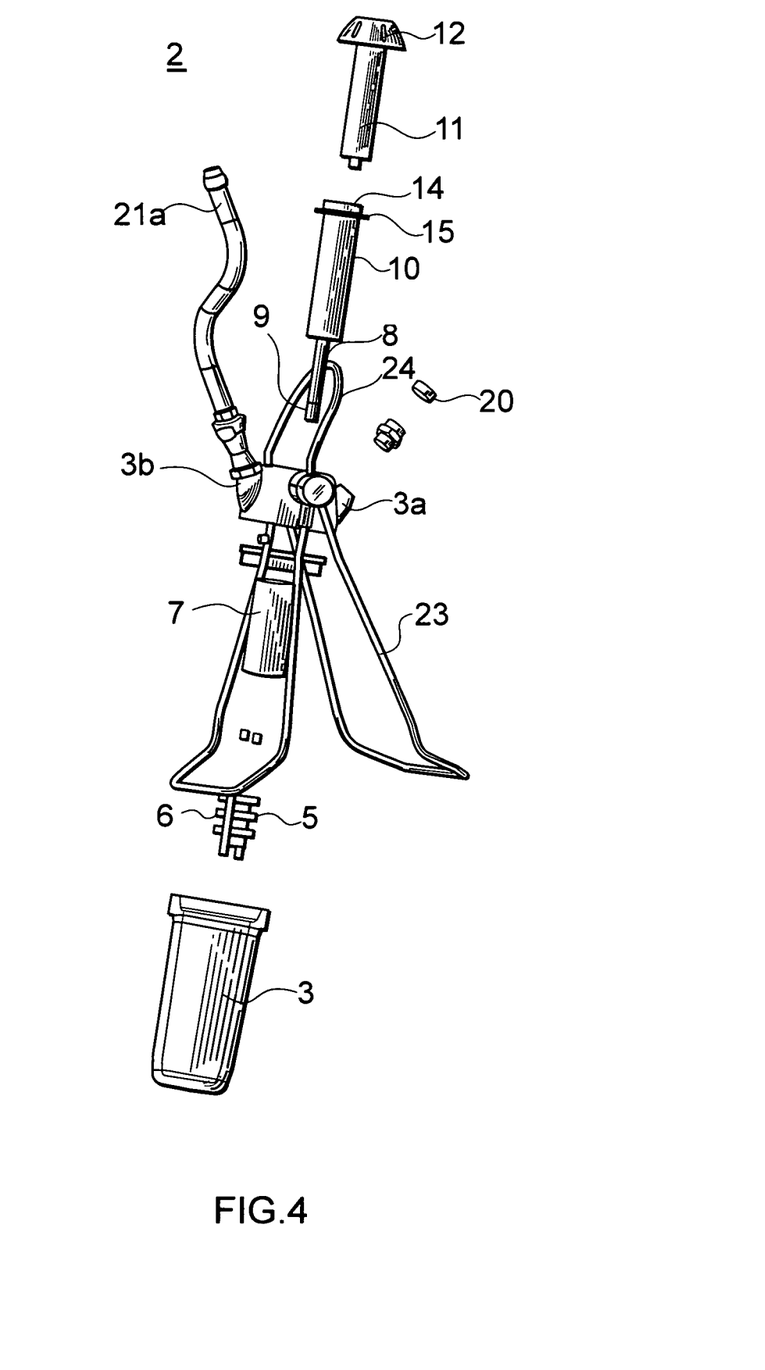
FIG. 4 is an exploded view of the delivery unit shown in FIG. 1.

The user can then gently screw the cartridge 11a number of turns into the unit 2 until the cartridge head 17 is supported by the cartridge head holder 10 and the piercing pin 18 punctures the cartridge outlet 19. The resulting flow of gas from the cartridge 11 produces a bubbling effect in the water, which may be viewed by the user in the fill container 3.

Essentially, the gas flow passes through the delivery tube 8 and exits at the jet delivery assembly 9 to enter the water. As the released gas bubbles upward, such motion causes the flowing of both the gas and the water through the conical baffles 5 in the mixing unit 4. The unique and efficient geometrical configuration and positioning of the conical mixing elements 5 within the mixing unit 4 guide and enhance fluid flow resulting in an efficient mixing and a substantially homogeneous dispersion of the gas with the water. Such mixing is accomplished efficiently without the need for any moving parts, using highly simple and economical parts. The pressure of the gas flow may be controlled or reduced by the aforementioned pressure regulating valve to a specified pressure, in order to achieve a desired mixing efficiency.

Figure 1:
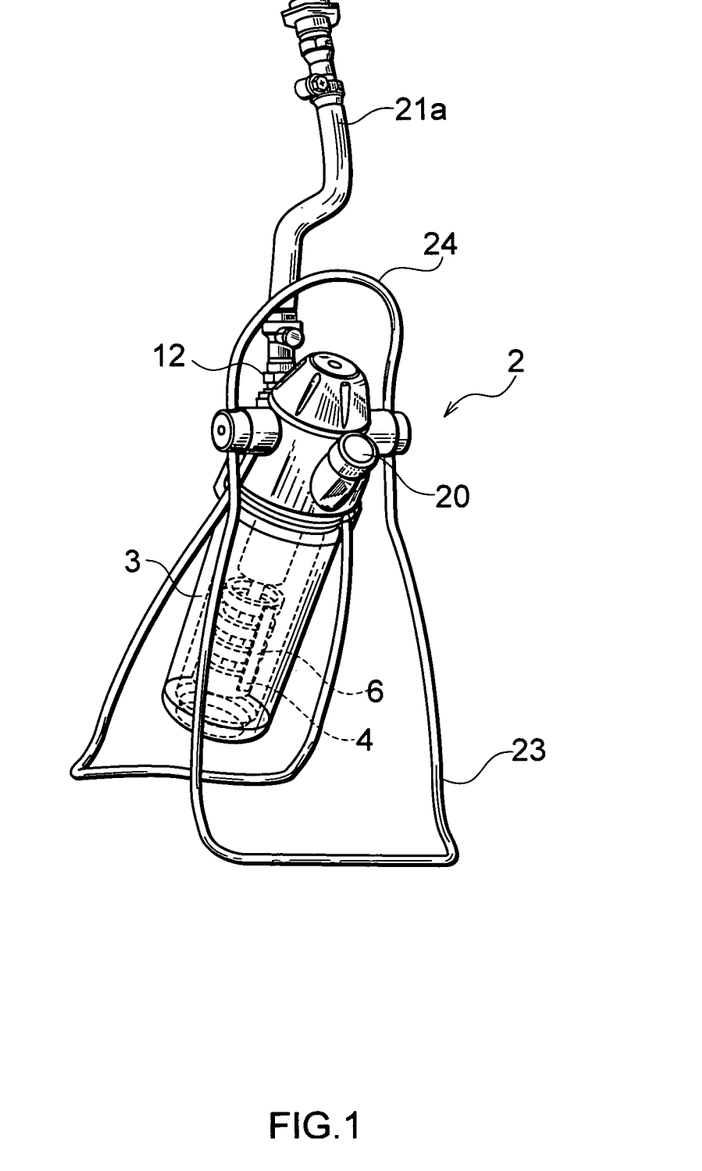
FIG. 1 is a perspective view of the delivery unit of the mobile treatment apparatus of the subject invention.

It should be noted that the efficient mixing and proper dispersion is accomplished statically, due in large part to the release of the gas into the water at the bottom of the fill container 3, and the bubbling upward of the released gas through the mixing unit 4. Thus, although the delivery unit 2 can be easily carried and placed on a convenient surface, a severe tilting or turning upside down of the unit may typically hinder or prevent this mixing process depending on the water fill level. It may be preferable for the fill container to have a tilt of no greater than 30° relative to a vertical position, as shown in FIG. 1.

The statically mixed gas-water dispersion produces a light, misty, fog-like mixture flowing toward the top of the fill container 3, usually consisting of a high concentration of $CO_2$. Thus, the fog-like mixture has a "dry", low humidity nature, but contains an even dispersion of loosely attached water (only about 5% or so of the filled water may actually be used), providing a highly desirable balance for the transdermal delivery of the $CO_2$ to the user.

The water vapor concentration of the resulting mixture should ideally be in the range of 40,000 ppm. The achievement for the appropriate balance of $CO_2$ with water for the effective transdermal delivery of, and treatments with, the gas is a key feature of the present invention. It was noted in subsequent testing using a "mini" version of the present invention (described below) using a 16 g cartridge, that when the pressure regulating valve was adjusted to allow the $CO_2$ to dispense from the cartridge for about 3 to 15 minutes, the treatments successfully provided health benefits, but when the $CO_2$ flow lasted less than 3 minutes or greater than 15 minutes, the treatments did not provide such health benefits. This finding indicates that when the $CO_2$ is dispensed too quickly, it is oversaturated with water. It also indicates that when the $CO_2$ is dispensed too slowly, there may not be enough momentum to reach the required water saturation level or "sweet spot" (approximately 40,000 ppm, as mentioned above) to be therapeutically effective and also, there may not be enough momentum to transfer the $CO_2$ effectively into the absorption suit. It is conceivable that, with gas cartridges of varying size having the same typical fill pressure of 8 MPa for the gas cartridges, the flow time can be proportionately increased/decreased according to the respective sizes of the gas cartridges, in order to achieve this "sweet spot" of approximately 40,000 ppm. For example, the time may be halved for a smaller, 8 g $CO_2$ cartridge or increased by approximately 6 times for a 93 g cartridge, etc.

The warmth of the fill water in the fill container 3 may further enhance the gas flow and the resultant dispersion. A temperature label, thermometer or other means commonly known in the art can be provided on or with the apparatus 1 to ensure the use of water of a suitable warm temperature.

The misty, fog-like mixture then flows through the flexible tubing 21 to the sealed absorption suit 22, where it provides a highly effective and efficient therapeutic treatment of the user's body through the skin, with the a correct gas-water mixture balance.

Upon completion of the treatment session, when the bubbling flow of gas can no longer be seen in the fill container 3, the user can easily detach the tubing 21 from the suit 22, and remove the empty gas cartridge 11 from the delivery unit 2, for disposal. The remaining fill water may be reused for subsequent treatments, or the delivery unit 2 may be easily washed and re-filled with water.

Mini Version

Figure 5:
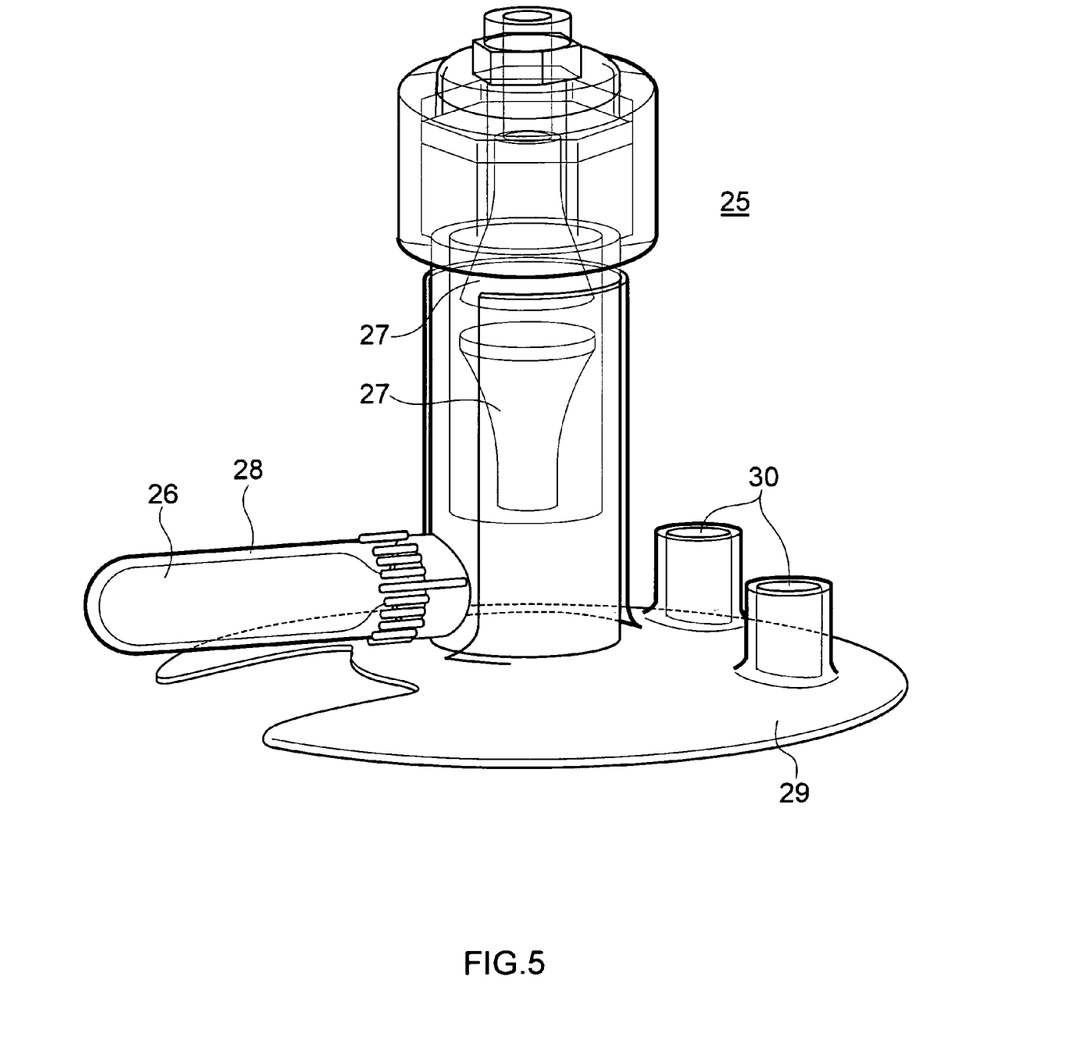
FIG. 5 is a partially transparent, assembled perspective view of another, mini embodiment of the delivery unit of the subject invention.
Figure 6:
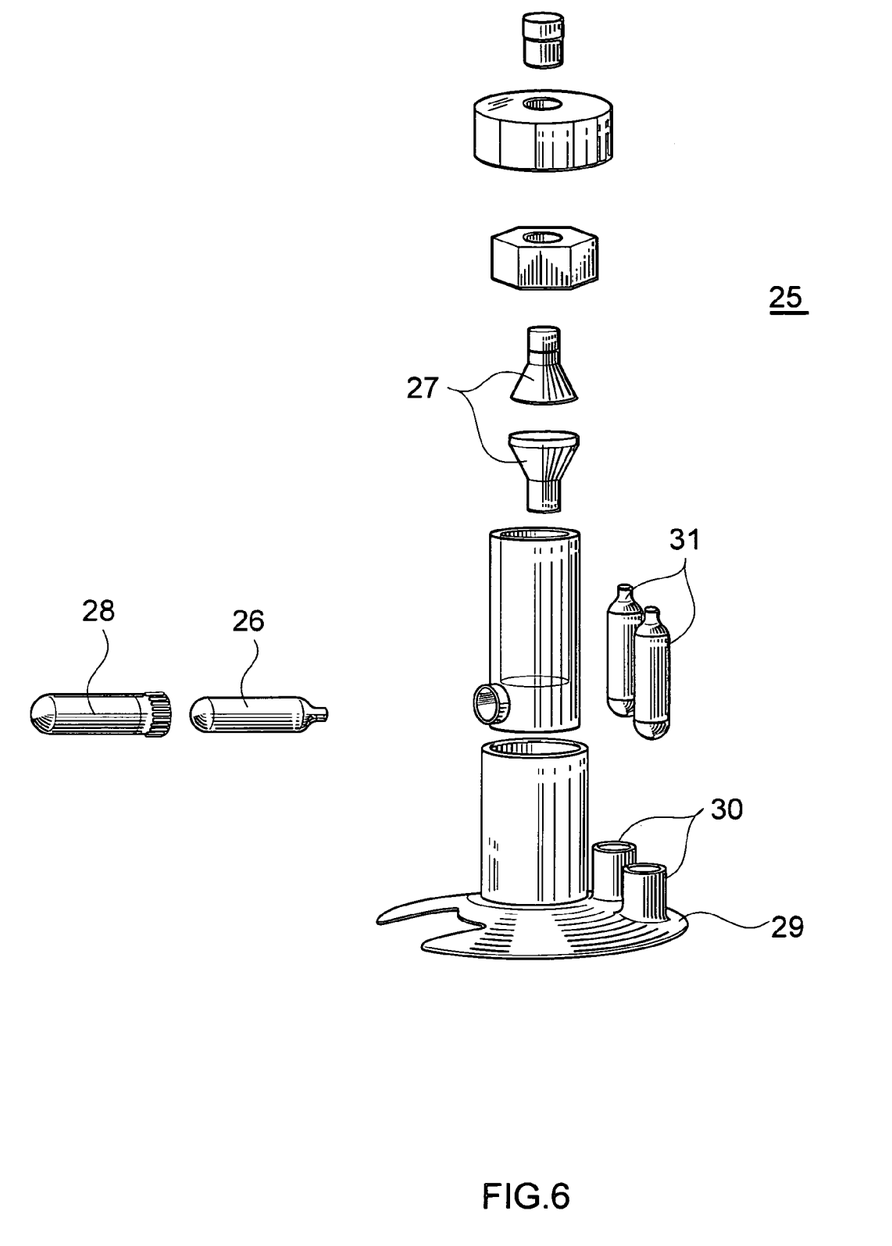
FIG. 6 is an exploded view of the delivery unit of the other embodiment shown in FIG. 5.

In another and more cost effective embodiment of the mobile treatment apparatus of the present invention, a smaller delivery unit 25 may be used, as shown in FIGS. 5 and 6. This smaller version may be only several inches in height and is even more conveniently portable than the above-described version. This embodiment uses essentially the same concepts as the above-described embodiment. However, the required gas cartridge 26 is of a smaller size and capacity. For example, the gas cartridges may be of standard sizes that contain 16 g, 8 g or only 1.3 g of the $CO_2$ gas, at a fill pressure of 8 MPa for each. Such cartridges may have dimensions of approximately 4 inches length×0.5 inch diameter, 3 inches length×0.5 inch diameter, or 1.5 inches× 0.25 inch diameter, respectively. The water temperatures for this embodiment may typically be in the range of 10-70 C.

The conical mixing elements 27 in this case are two conical shaped elements, where the bases of the elements may be facing each other, although other arrangements of the conical elements commonly known in the art are also possible. The central point apertures of the conical shaped elements allow gas/water flows therethrough, thereby achieving the static mixing of the gas and water.

The gas cartridge 26 in this case can be enclosed by a protective sleeve 28 for the user to grasp, and the cartridge may be horizontally inserted at the bottom of the delivery unit 25 for the gas flow to rise through the centers of the baffles 27 to mix homogenously with the water, and the resultant gas-water mixture exits the delivery unit 25 at the top.

Again, as described for the above version, the released gas enters the filled water at the bottom of the delivery unit 25, in order to bubble upward and provide static mixing and a substantially homogeneous dispersion of the gas with the water. Thus, a severe tilting or inversion of the unit may impede or prevent this process, and it may be preferable for the delivery unit 25 to be in a vertical position as shown in FIG. 5 or tilted to a maximum of about 30° from the vertical position.

The absorption suit connected to this "mini" version typically has a smaller size and capacity, as well, and may be adapted to be particularly suitable for the treatment of smaller, partial portions of the body, such as the hands, feet or elbows. This is of course highly advantageous when only such partial portions, rather than an entire lower body for example, require therapy, such as patients with arthritic pains in only the hands, etc.

Figure 7:
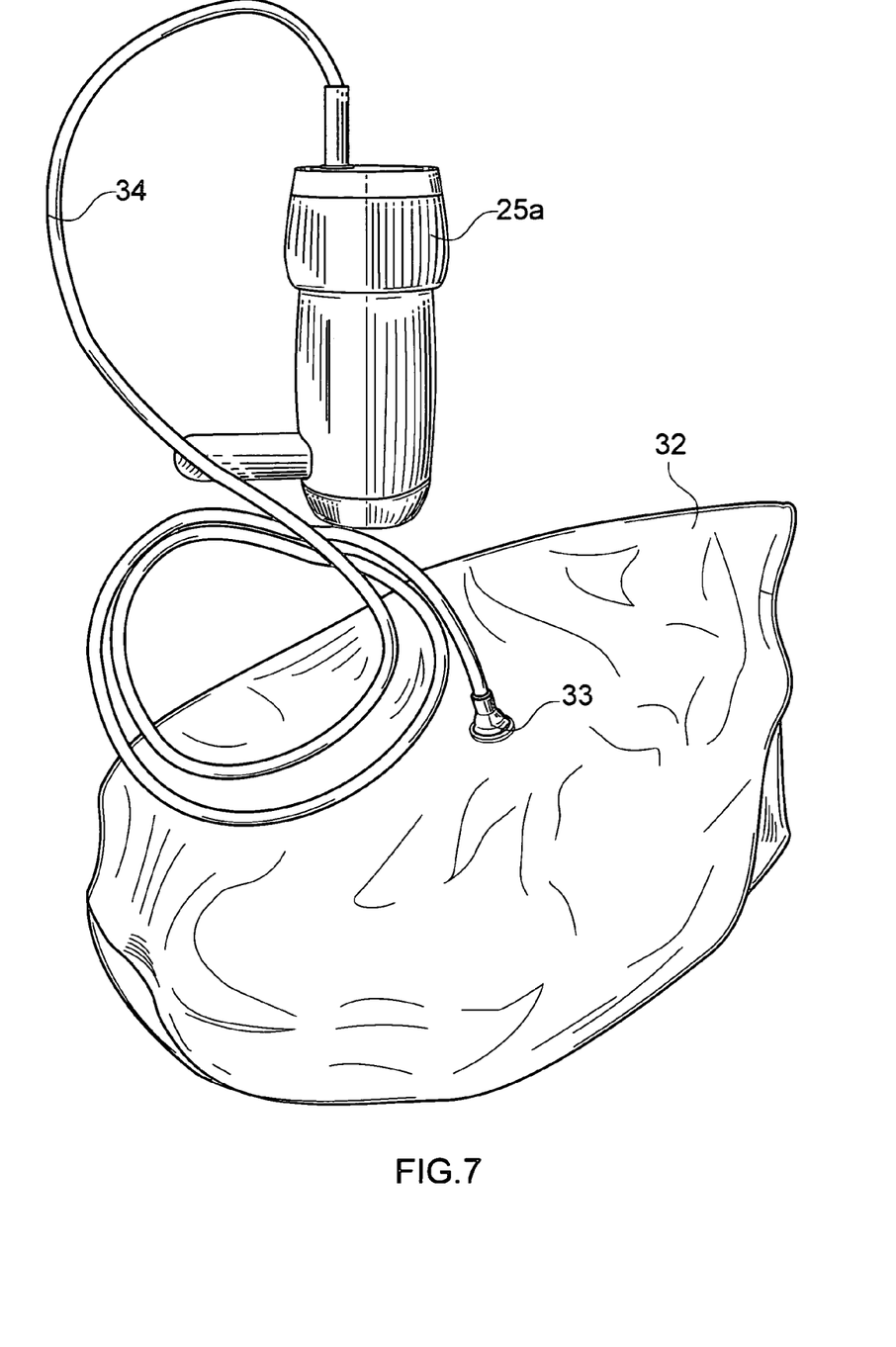
FIG. 7 is a perspective view of a mini embodiment of the mobile treatment apparatus of the present invention.
Figure 8:
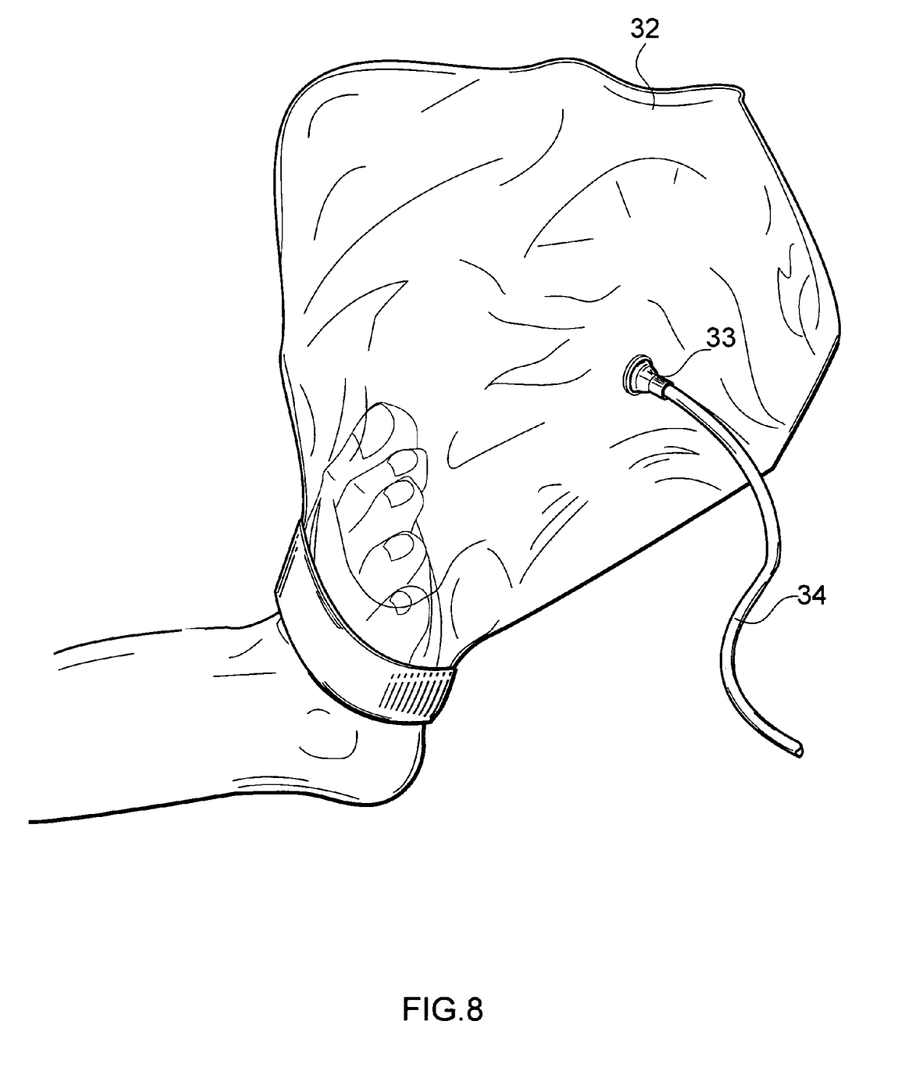
FIG. 8 is a perspective view showing a partial treat suit of the mini embodiment covering the right toes and forefoot of a patient.

As an example, such a "partial" treat suit may be made of a transparent polyethylene material in a rectangular shape. The treat suit may be disposable, and may have different sizes to accommodate a user's hand, foot, finger, hip, waist, scalp and so on as needed. FIG. 7 shows an example of such a partial treat suit 32 connected to a delivery unit 25a of a version of the mini device, and FIG. 8 shows the treat suit 32 covering the toes of a user's right foot, in preparation for treatment. A hole 33 may be punctured in the treat suit 32, with the hole reinforced with a thicker polyethylene material, so that the flexible delivery tube 34 from the delivery unit 25a may be plugged into the hole 33, for delivery of the gas-water mixture to the suit 32. A small flap (not shown) may be disposed at the inner side of the hole 33, wherein the flap may be formed of the same reinforced material, so that the flap opens and closes respectively upon the plugging in and unplugging of the delivery tube 34.

The delivery unit 25 may be provided with a lightweight stand 29, having thereon circular stands 30 to hold additional small gas cartridges 31 that may be needed as shown in FIG. 6.

Absorption of Carbon Dioxide Through the Skin

With the above-described systems, one can achieve effective and efficient deliveries of pharmaceutical, medical or purified $CO_2$ gas to the user. Such systems for artificially and enhancing the positive effects of $CO_2$ balneotherapy has a long history as a well-known therapy in Europe, Japan and mainly Germany. These therapies have had at least 120 years of success at healthcare establishments for treating major conditions such as cardiovascular conditions (high blood pressure and atherosclerosis), diabetes mellitus, arthritis, and osteoporosis without side effects.

Furthermore, as stated above, scientists and researchers have recently been exploring ways of delivering drugs, such as medical gases, to the patient through the skin, which can be a safer, non-invasive method of delivery. Transdermal drug delivery offers numerous advantages over more traditional drug delivery forms. It can avoid problems caused by oral dosages, such as gastrointestinal irritations, drug metabolism issues and interference due to the presence of food, and it may be administered to nauseated or unconscious patients. Transdermal methods are non-invasive compared to intravenous means and, due to the steady diffusion of the drug through the skin, they offer more consistent drug infusions, even in localized areas over several days, thereby reducing "peaks" that may cause side effect. Transdermal delivery is simpler and painless for patients and thus, more likely to achieve patient adherence to therapy regimens. Due to such advantages, innovations in transdermal drug delivery methods have been increasing in recent years.

However, a disadvantage of such drug delivery is that skin typically has a natural "barrier function" to prevent foreign substances from entering the body. Indeed, skin evolved for the purpose of protecting against unwanted substances such as toxins and microorganisms. Thus, drug absorption through the skin is difficult, and an effective transdermal delivery system must find ways to efficiently pass through this barrier.

$CO_2$ gases, on the other hand, are especially suited to such transdermal drug deliveries without side effects such as localized irritations. This is because $CO_2$ has 25 times greater permeability to cell membranes than does oxygen. $CO_2$ also easily dissolves into oil. Skin has a structure similar to that of water and oil, which may explain why skin can also easily absorb $CO_2$.

Although transdermally absorbed carbon may be referred to as "carbon dioxide gas", in fact, the absorbed $CO_2$ is actually not in the form of visible bubbles. Instead, transdermally absorbed carbon dioxide exists in the form of invisible water-dissolved molecular $CO_2$. The positive medical effects described above are obtained through exposure to this molecular $CO_2$. For example, if one simply blows $CO_2$ bubbles from a tube onto the skin, no cosmetic effects can be obtained because the $CO_2$ is hardly absorbed into the skin in the form of bubbles.

In the present invention, the above-described mixture of gas and water should typically have a weak acidity of about 4 pH. This is because the lower the pH is, the more the $CO_2$ exists in the above-mentioned molecular state, which is desirable for its excellent transdermal absorption characteristics. Indeed, if the pH of the mixture is high, $CO_2$ in water tends to change to carbonic acid ($H_2CO_3$) and bicarbonate ions, which are not easily absorbed through the skin. It is important to the features of the present invention to distinguish between this carbonic acid ("carbonated water") and $CO_2$ in the molecular state.

If the pH is 8, for example, 98% of the dissolved $CO_2$ may dissociate to generate ions, and only a small amount of the $CO_2$ becomes absorbed transdermally. On the other hand, of the pH is too low, $CO_2$ has difficulty dissolving into the molecular state and also, the mixture becomes a strong acidic carbonated water which may stimulate any wound on the skin that one is trying to heal.

$CO_2$ increases tissue oxygen, due to the oxygen conveyance protein called hemoglobin contained in red blood cells, as well as the Bohr effect. The supply of oxygen for supporting the activities of a creature is mainly performed by hemoglobin in red blood cells. After oxygen binds to the hemoglobin in the lungs, it is released in the tissues. In the presence of increased $CO_2$ in the blood within the tissues, the pH in the tissues decreases due to the conversion of the $CO_2$ to bicarbonate molecules and acidic protons. With decreased pH, the oxygen more easily dissociates from the hemoglobin. This reduction in oxygen affinity to hemoglobin is referred to as the "Bohr effect". Due to this effect, the increased oxygen dumping in the tissues results in the many positive medical effects described above.

Various research studies conducted in Europe have confirmed that $CO_2$ absorbed in this manner has positive effects such as blood vessel dilations leading to healthier skin, greater oxygen supply to the cells resulting the activation of cell metabolisms and improvements in skin texture, and anti-aging, and wound healing effects. Furthermore, studies have shown that the addition of mineral salts and/or essential oils, or other additional substances, to the water may further enhance the positive effects of CO balneotherapy.

In addition to the treatment of major conditions that affect millions of people around the globe, the above-described purified $CO_2$ gas therapies have many other positive effects on the human organism, including exercising and refreshing the body, strengthening internal organ functions, relaxation and stress reduction benefits, anti-bacterial and blood cleansing tendencies, muscle and nervous system stimulations, skin beautification effects, etc.

The present invention thus provides a highly simple means for the transdermal delivery of $CO_2$ or other such biologically beneficial gases, utilizing a device that is very simple and cost effective to manufacture and to use. The apparatus of the present invention requires no electricity or technical assistance to operate, leaves no residuals, and is easy to clean and maintain. It is conveniently small in size and mobile. It is equally applicable for both commercial and home usage, and makes therapeutic treatments as easy, pleasant and relaxing as taking a warm bath.

Medical Test Results

Medical tests were conducted, both before and after the above-mentioned $CO_2$ treatment, using an apparatus as described above in the mini device embodiment. The diagnostic tools used for testing were the SensiLase® System for testing of circulation in the extremities and the AcQtrac™ System for circulatory testing, which are FDA approved and CE marked noninvasive tools by Vasamed®.

In a first set of tests, a mini embodiment as described above was used with a 16 g $CO_2$ cartridge, under the pH, temperature and other conditions generally described above and as illustrated in FIG. 7. The patient had a skin graft all over the lower right leg and exhibited the bad injury but with a good skin condition. The partial treat suit 32 was sealed over the right toes and forefoot of the patient, as illustrated in FIG. 8, and the SensiLase® System was used to measure both Skin Perfusion Pressure (SPP) which assesses microcirculation and Pulse Volume Recording (PVR) which assesses macrocirculation, at a middle toe on the right foot. A first measurement of SPP was taken immediately prior to the $CO_2$ treatment, after which the 16 g of $CO_2$ was caused to flow into the device and the gas-water mixture filled and inflated the treat suit. After the gas cartridge emptied and the treat suit deflated, a second measurement was taken. A third measurement for SPP was taken approximately 12 minutes after the $CO_2$ treatment.

An SPP of less than 30 indicates possible critical limb ischemia (CLI) and a non-healing wound. An SPP higher than 30 indicates that wound healing is likely. As summarized in Table I below, the SPP measurements showed a potentially unhealthy microcirculation with an SPP of 19 mm Hg prior to the treatment. However, the SPP improved significantly to reach an almost normal value of 29 mm Hg immediately after the treatment, and 12 minutes later, the SPP continued to rise to an impressive 52 mm Hg. Subsequent testing revealed that the SPP values may continue such improvements even for days after a single $CO_2$ treatment. Similarly, the PVR assessments made both before and after the $CO_2$ treatments also revealed an impressive improvement from a non-wound healing to a wound healing condition. Thus, one could conclude that a single application of the $CO_2$ delivery system as described above can produce a very significant improvement in the vascular condition of the patient.

TABLE I

| SPP Measurement Time (approx.) Date: Nov. 22, 2007 | SPP Value (mm Hg) <30 CLI, non-healing wound >30 Wound healing likely |
|---|---|
| 1) Immediately prior to $CO_2$ treatment | 19 |
| 2) Approximately 7 minutes after $CO_2$ treatment | 29 |
| 3) Approximately 12 minutes after $CO_2$ treatment | 52 |

In another sample medical test, the AcQtrac™ System was used at the various time points as summarized below in Table II, to measure blood pressure (BP) and evaluate cardiovascular health. The patient was a 50-year-old male with a height of 157 cm (5 foot 2 inches) and a weight of 88 kg (194 pounds). Since a normal blood pressure should generally be below 120/80 mm Hg, Table II indicates that prior to the $CO_2$ therapy, the patient exhibited mild hypertension with a BP of 162/99 mm Hg. However, immediately after a single treatment (typically lasting about 5 minutes, as mentioned previously), the BP had lowered significantly to within a healthy range, at 148/101 mm Hg. This healthy BP level continued even more than 30 minutes after the treatment and, in fact, continued to go down to 137/89 mm Hg at that point.

TABLE II

| Blood Pressure Measurement Time Date: Nov. 23, 2007 | Blood Pressure Value (mm Hg) <120/80 optimal |
|---|---|
| 15:57:31 (immed. before $CO_2$ treatment) | 162/99 |
| 16:08:58 (immed. after $CO_2$ treatment) | 148/101 |
| 16:16:32 | 148/96 |
| 16:18:47 | 149/91 |
| 16:38:43 | 137/89 |

Thus, the clinical tests show that even a single $CO_2$ treatment using the devices of the present invention can provide significant hemodynamic health and wound healing benefits to the patient, in a simple, safe and noninvasive manner. Indeed, the present invention may represent a breakthrough in healthcare by safely delivering a gas as a pharmaceutical/medical substance through the skin barrier and achieving significant health benefits, without the risk of side effects arising from other medical treatments such as surgeries.

Other Embodiments

Additionally, due to the increase in tissue oxygen resulting from the Bohr effect described above, it is conceivable that the above-described treatments and treat suits may also be applied to animals as well as humans, for similar health benefits.

It should also be noted that the present invention is intended to encompass the possibility of adding other pharmaceutical substances, such as insulin, into the gas-water mixture for delivery into the human body or into animals. In this manner, such pharmaceutical substances could enter through the pores of the skin and into the blood stream and could even be targeted to treat certain body parts or organs.

For example, it is well known that the insulin molecule is too large to be transferred with conventional syringe needles. However, the skin pores of most people are large enough to receive this drug compound via the apparatus of the present invention. Thus, an important feature of the present invention is to safely and noninvasively "break" the natural skin barriers by opening up the skin pores to create an effective transdermal drug delivery method.

It is further encompassed within the present invention that the apparatus and its "mini" version is scalable. For example, an even smaller-sized version using a small gas cartridge may be provided, for delivering the above-mentioned or other pharmaceutical/medical substances only to a small body part, such as a finger. Besides insulin, any other compounds that are soluble in water and can bind with the $CO_2$-water mixture for transfer into the treat suits could be used. In such cases, the user automatically benefits from any accompanying health effects that result from the $CO_2$ entering the body, as well as from the additional compounds.

It is also encompassed within the present invention that the apparatus may be used to deliver the fog-like mixture to the skin without the use of an absorption suit. Transdermal delivery of the $CO_2$ may be accomplished by "misting" the skin by holding an open end of the delivery tube (with the other end leading to the delivery unit) close to the skin (approximately 1 or 2 inches away, for example) or by "spraying" the skin with the high concentration of $CO_2$. The absorption suits may produce higher efficacies because they keep the fog-like mist around body parts for controllable periods. However, due to the above-described high skin permeability of $CO_2$, effective treatments may still occur without such suits.

Indeed, the $CO_2$ itself may be considered essentially a medical or pharmaceutical substance. The scope of the present invention can also encompass the use of a wide variety of medical, pharmaceutical or purified gases and related substances. In general, such gases present excellent opportunities for therapeutic innovations, because gases are important biological messenger molecules and show promising biological effects, naturally occurring gases appear to have low toxicity profiles, their properties may enable the application of other medical principles. Current uses of gases in medicine have been minimally explored. Thus, the present invention can provide an effective medical device or drug delivery device for the safe, non-invasive injection of medical gases into the human organism through the pores of the skin.

The foregoing description of the embodiments of this invention has been presented for purposes of illustration and description. It is not intended to be exhaustive or to limit the embodiments of the invention to the form disclosed, and, obviously, many modifications and variations are possible. As an example, while the above-described embodiments use a "dry" version using very little water, the delivery unit 2 of the present invention can also be configured for a "wet" version, wherein the delivery unit 2 is placed within open water such as in a bath. Various apertures or inlets at the mixing chamber permit the open water to flow into the mixing chamber, as drawn in by the gas flow from the $CO_2$ cartridge. A combination of static mixing elements such as the above-described cone-shaped pieces or baffles arranged at the walls of the mixing chamber, etc. may cause the channeling/subdividing/stretching/diffusion of the water and gas flows, to achieve a desired and even gas-water dispersion within the open water. In this manner, for example, bathtub water may be enriched with $CO_2$ for a healing bath, providing convenient treatments using an apparatus that is lightweight, low cost, virtually maintenance-free and uses no electricity. Additions such as minerals, salts and essential oils may also be applied to the open water to increase treatment efficacy.

Furthermore, the present invention may even have diversified application possibilities, including those in preventive medicine, sports medicine, veterinary medicine, the space biomedical industry (e.g., muscle and bone less in space), rehabilitation medicine, and troop health support for the military. One may also foresee additional applications of the dispersion technologies of the present invention in fields such as waste water treatment and gas-liquid dispersions (i.e., as a soft drink production alternative). Such modifications and variations that may be apparent to a person skilled in the art are intended to be included within the scope of this invention as defined by the accompanying claims.

What is claimed is:

1. A mobile therapeutic apparatus for use in treating a user of the apparatus with medical or therapeutic gases, comprising:
    a container having an interior water reservoir;
    a mixing unit having a motionless mixer positioned within the interior water reservoir and a gas receiver;
    a gas cartridge unit removably mounted to said mixing unit and fluidically connected to the mixing unit via the gas receiver, wherein a humidification control valve regulates a mixing rate of a gas from the cartridge with water retained in the interior water reservoir, to achieve a specified gas-water mixture comprising a humidified gas that is effective for transdermal delivery of the humidified gas to said user; and
    a wearable receiver suit sized and shaped to form a space around at least an area of the user's body to be treated, wherein said suit is fluidically connected to said mixing unit, and configured for delivery of said humidified gas from said mixing unit to said space to treat said area via said transdermal delivery;
    wherein the motionless mixer includes a gas conduit extending into the interior water reservoir from the gas receiver to a position within the water reservoir on a generally oppositeside with respect to a humidified gas exit conduit.

2. The mobile therapeutic apparatus of claim 1, wherein said humidified gas is a CO2 gas and said resulting gas-water mixture contains a concentration of $CO_2$ effective for transdermal delivery in treating said area.

3. The mobile therapeutic apparatus of claim 1, wherein the humidified gas is a misty, fog-like mixture having a water vapor concentration of approximately 40,000 ppm.

4. The mobile therapeutic apparatus of claim 1, wherein the gas-water mixture has a pH of about 4.

5. The mobile therapeutic apparatus of claim 1, wherein the temperature of the water ranges from 35-70 C.

6. The mobile therapeutic apparatus of claim 1, wherein said gas-water mixture has a saturation level which is effective for transdermal delivery in treating said area.

7. The mobile therapeutic apparatus of claim 1, wherein said motionless mixer comprises at least one cone-shaped baffle having an aperture at its central point wherein, when positioned within the water reservoir, the at least one cone-shaped baffle is at least partially submerged in water, the at least one cone-shaped baffle having side walls providing mixing of gas and water as the gas-water mixture flows through said aperture.

8. The mobile therapeutic apparatus of claim 1, wherein said motionless mixer comprises a plurality of cone-shaped baffles wherein their central points are aligned along a single axis.

9. The mobile therapeutic apparatus of claim 1, wherein said flow of gas from the cartridge induces a mixing with the water through said mixer and also induces the delivery of the gas to the wearable receiver suit.

10. The mobile therapeutic apparatus of claim 1, wherein the gas cartridge can be activated by screwing the cartridge into the apparatus, causing a cartridge piercing module of the mobile therapeutic apparatus to pierce the gas cartridge.

11. The mobile therapeutic apparatus of claim 1, further comprising a pressure-relief means, at a fill opening for filling the mixing unit with the water, for regulating pressure within the mixing unit.

12. The mobile therapeutic apparatus of claim 1, wherein the gas-water mixture has a homogeneous dispersion of the gas.

13. The mobile therapeutic apparatus of claim 1, wherein the gas-water mixture further comprises another pharmaceutical substance for transdermal delivery to the user.

14. A method of non-invasively treating an area of an individual user with medical or therapeutic gases, the method comprising:
    filling a container of a mobile therapeutic apparatus with water, having a mixing unit including a motionless mixer at least partially submerged in the water, the motionless mixer including a gas conduit extending into the container from a gas cartridge receiver to a position within the container on a generally opposite side with respect to a humidified gas exit conduit;
    fitting a wearable receiver suit, fluidically connected to said mixing unit via said humidified gas exit conduit, and sized and shaped to form a space around at least an area of the user's body to be treated, to the area of the user's body;
    removably mounting a gas cartridge to said mixing unit via a gas cartridge receiver,
    wherein a humidification control valve regulates a mixing rate of a gas from the cartridge with water retained in the container, to achieve a specified gas-water mixture that is effective for non-invasive transdermal delivery of humidified gas to said user; and
    delivering the humidified gas to the receiver suit, to treat said area via said non-invasive transdermal delivery.

15. The treatment method of claim 14, wherein the gas-water mixture is a misty, fog-like mixture having a water vapor concentration of approximately 40,000 ppm.

16. The treatment method of claim 15, wherein said humidified gas is a pharmaceutical or medical substance for transdermal delivery to the user.

17. The treatment method of claim 15, wherein said method improves a blood circulation condition and a cardiovascular condition in the user.

18. The treatment method of claim 15, wherein said method treats a chronic or an acute disease of the human body.

19. The mobile therapeutic apparatus of claim 1, wherein a cartridge head holder is positioned between the cartridge and the gas cartridge receiver.

20. The mobile therapeutic apparatus of claim 1, wherein the wearable receiver suit is configured for non-invasive delivery of said humidified gas from said mixing unit to said space to non-invasively treat said area via said transdermal delivery, and wherein said mixing unit is configured to achieve a specified gas-water mixture comprising a humidified gas that is effective for non-invasive transdermal delivery of the humidified gas to said user.

\* \* \* \* \*